United States Patent [19]
Myers et al.

[11] 4,164,407
[45] Aug. 14, 1979

[54] BENZOXAZINE HERBICIDES

[75] Inventors: Stewart W. Myers, Morristown; Homer K. Spencer, Randolph, both of N.J.

[73] Assignee: Sandoz, Inc., East Hanover, N.J.

[21] Appl. No.: 840,227

[22] Filed: Oct. 7, 1977

[51] Int. Cl.$^2$ .................... A01N 9/22; C07D 265/18
[52] U.S. Cl. .......................................... 71/88; 544/90
[58] Field of Search .............................. 544/90; 71/88

[56] References Cited

U.S. PATENT DOCUMENTS 3,417,085  12/1968  Kuch et al. ............................ 544/90

OTHER PUBLICATIONS

Boots, "J. Med. Chem.", vol. 12, (1969), pp. 426–428.
Boots et al., "J. Med. Chem.", vol. 13, (1970), p. 144.
Boots et al., "J. Med. Chem.", vol. 15, (1972), 330–332.

*Primary Examiner*—Natalie Trousof
*Assistant Examiner*—R. W. Ramsuer
*Attorney, Agent, or Firm*—Gerald D. Sharkin; Richard E. Vila; Frederick H. Weinfeldt

[57] ABSTRACT

2-amino-4H-3,1 benzoxazines, e.g. 6-chloro 2-dimethylamino-4H, 3,1-benzoxazine, are useful as herbicides. The compounds may be prepared by reacting an amine with a 2-halomethylphenyl isocyanate.

20 Claims, No Drawings

BENZOXAZINE HERBICIDES

This invention relates to benzoxazine compounds and more particularly to 2-amino-4H-3,1-benzoxazines, and to the use of the compounds as herbicides and composition containing said compounds as well as to method for the preparation of the compounds and intermediates in the preparation thereof.

The compounds of this invention are (A) free bases which may conveniently be represented by the formula I:

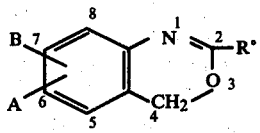

wherein each of A and B is independently, a hydrogen atom or halo having an atomic weight of from about 34 to 80, ie chloro or bromo, provided that both A and B are not hydrogen atoms, $R^0$ is a member of the class consisting of:
(a) tertiary-amino of the formula:

wherein each of $R^1$ and $R^2$, independently, is alkyl having from 1 to 6 carbon atoms, or alkenyl having from 3 to 6 carbon atoms, provided that the ethylenically unsaturated bond is not on the carbon atom adjacent to the nitrogen atom;

(b) cycloamino of the formula:

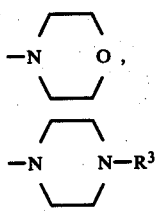

wherein $R^3$ is alkyl having from 1 to 3 carbon atoms, or

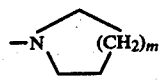

wherein m is a whole integer of from 1 to 3;

(c) tertiary butylamine,

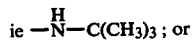

(d) N-alkyl, N-cyanoalkylamino, of the formula

in which $R^4$ is alkyl having from 1 to 3 carbon atoms and n is 1 or 2; or (B) acid addition salts thereof.

Compounds I may be obtained by reacting (process a) an 2-halomethylphenyl isocyanate (a compound II) of the formula

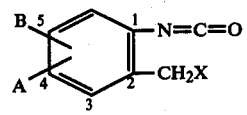

in which A and B are as defined above, and X is chloro or bromo ie a halogen having an atomic weight of from about 34 to 80; preferably bromo, with an amine (a compound III) of the formula $$H-R^0 \quad \text{III}$$

in which $R^0$ is as defined above. Process (a) may be carried out in an inert organic solvent, eg an aromatic hydrocarbon, such as toluene, at a moderate temperature, eg from about 20° to 120° C., preferably from about 40° to 80° C., and under essentially anhydrous conditions. It is preferred; but not critical, that the reactants (compounds II and III) be present in about equal equivalents, as use of an excess of the amine (III) tends to increase the formation of undesirable by-products.

Compounds II are obtainable by phosgenation (process b) of a corresponding 2-halomethyl aniline salt (a compound IV) of the formula:

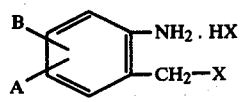

in which A, B and X are as defined above. The phosgenation may be carried out by reacting a compound IV with phosgene in an inert organic solvent, eg. an aromatic hydrocarbon such as benzene, eg from about 8 to 20% phosgene in solvent, eg 12.5% phosgene in benzene, at temperatures, eg of from about 70° to 120° C., preferably at the reflux temperature of the solvent, under essentially anhydrous conditions.

Compounds IV are obtainable by halogenating a corresponding 2-hydroxymethyl aniline, ie. a Compound V of the formula:

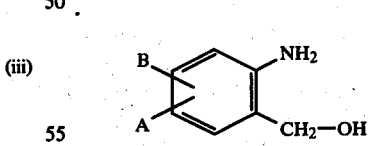

in which A and B are as defined above. The halogenation (process c) is conveniently carried out by treating a compound V with a halogenating agent in the conventional manner; e.g. when X=Br, using hydrobromic acid, eg. 48% HBr in water, and when X=Cl, the chlorination may be accomplished in the customary manner for halogenating a primary hydroxy group associated with an aryl ring, e.g. by treatment of the hydrochloride salt of V with thionyl chloride at an elevated temperature e.g. at reflux. Convenient temperatures for process (c) when using hydrobromic acid are from about 80° to 100° C., preferably about 100° C., a solvent not being critical to the reaction, as the hydrobromic acid serves as the reaction medium. It is preferred that X is bromo, as the use of hydrobromic acid is particularly convenient.

Compounds V are obtainable by reducing the carboxylic function of a corresponding anthranilic acid, ie a Compound VI,

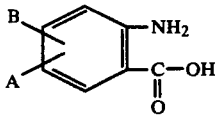
VI in which A and B are as defined above. The reduction (process d) may be accomplished by means conventionally employed in reducing a carboxylic function to a hydroxymethyl group. For example, a complex metal hydride (a compound VII) may be employed as the reducing agent, eg lithium aluminum hydride, in an aprotic medium, eg a cyclic ether, such as tetrahydrofuran under essentially anhydrous conditions. While the temperature at which the reduction is carried out is not critical, particularly convenient temperatures are from about 20° to 70° C., preferably from about 40° to 60° C., eg at the reflex temperature of the reaction medium.

An alternative method of obtaining compounds II, particularly those in which X is chloro, comprises first treating an o-methyl aniline (IVa)

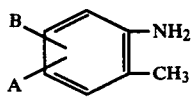
IVa in which A and B are as defined above, with phosgene (process b') to form the corresponding o-tolyl isocyanate IIa

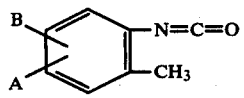
IIa in which A and B are as defined above. Process b' may be carried out under the same conditions as described above (b). process b).

The thus-formed compound IIa is then halogenated (process b'') to obtain the corresponding Compound II. The halogenation may be accomplished by employing anhydrous chlorine or bromine at a temperature of about 75° to 150° C. preferably 100° to 150° C. An inert solvent, such as higher halogenated hydrocarbons, for example, 1,1,2,2-tetrachloroethane, may be used; but it is preferred that the reaction be carried out in an excess of a compound of formula (IIa). The time is not critical, but it is preferred that the reaction be carried out for from 10 minutes to 5 hrs. It is preferred that the reaction be carried out in the presence of a light radiation source or a free radical initiator such as azobisisobutylnitrile, dibenzoyl peroxide and the like.

If desired, process (a) may be carried out in two steps, ie compound II may be reacted with an amine (III) as in process (a), but halting the reaction to obtain an intermediate urea (ie a Compound IIb)

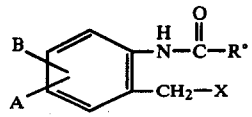
IIb in which A and B $R^0$ and X are as defined above, which upon further heating (under the conditions of process (a) is converted to the corresponding compound I.

Compounds IIb, are more readily separated when X=Cl, as the bromo analogs tend to react readily in situ to form the corresponding compounds I. Carrying out process (a) at the lower temperature range, eg from about 20° to 30° C. favors recovery of compounds IIb (process a') which can be isolated and when heated to the upper temperature range eg from about 35° to 120° are converted to the corresponding Compounds I, (process a''), which is conveniently carried out in an inert organic solvent eg a lower ketone or alcohol, such as acetone or ethanol, or toluene. It is preferred to include a mild base. While the mild base may be an organic base, eg a tertiary amine, such as triethyl amine or pyridine, it is preferred that the mild base be a salt of a strong inorganic base and a weak acid. Suitable cations are contributed by alkali metals, such as sodium or potassium, while the anion is suitably contributed by a weak acid, ie those having a pK value of about $5 \times 10^{-3}$ or less, such as acetic acid, preferably sodium acetate.

Reagents and reactants described herein, e.g., compounds II, III, IV, IVa, V, VI and VII are known and obtainable by known means, or where not known, may be obtained by adaptation of methods reported in the literature for the preparation of known analogs; many such compounds being commercially available.

The final products and intermediate compounds described herein may be recovered and refined, where such is desired, by conventional means, such as by crystallization, distillation or chromatographic techniques such as column or thin layer chromatography.

In those above-described reactions calling for anhydrous conditions, such may be achieved by means conventionally practiced where it is desired to essentially exclude moisture, e.g., by the use of absolute (dry) reaction medium and reagents, employing moisture-free apparatus and excluding moisture-laden air, e.g., by carrying out reactions in an atmosphere of inert gas and as nitrogen, or by use of moisture traps.

The above-described reactions are conveniently represented by Reaction scheme A presented below in which A, B, X and $R^0$ are as defined above.

REACTION SCHEME A

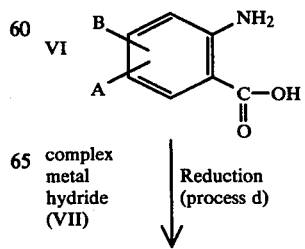

complex metal hydride (VII) | Reduction (process d)

-continued
REACTION SCHEME A

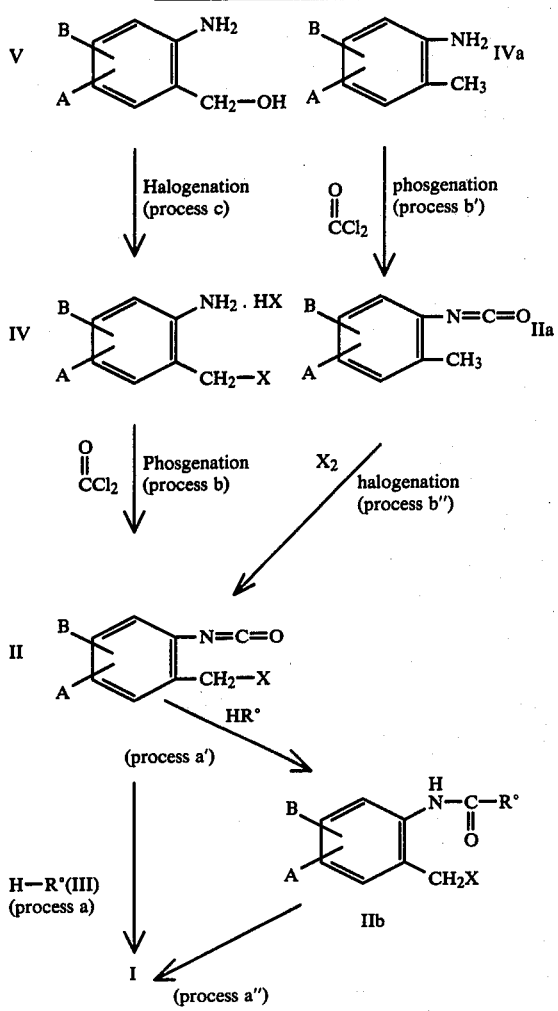

STATEMENT OF UTILITY

The compounds I are useful as herbicides as indicated by a wide spectrum of herbicide activity against both monocotyl and dicotyl plants including, for example, lepidium, agrostis, lolium, cucumis, and phaseolus. In general, the compounds I are indicated as exerting a stronger action against dicotyl plants than against monocotyl plant.

For general herbicidal use the amount to be applied to attain the desired effect will vary depending upon the plant involved and other standard variables such as the compound employed, mode of application, conditions of treatment and the like. However, in general, satisfactory results are usually obtained when the compound is applied at a rate in the range of from 1.0 to 10 kilograms per hectare, preferably from 1.5 to 7 kilograms per hectare. The compounds may be applied pre- or post-emergence with post emergence application being generally preferred.

The differential between the activity of the compounds I against dicotyl and monocotyl plants is of particularly interest in connection with certain preferred compounds I, in particular, those in which $R^0$ is of type (a) where $R^1$ and $R^2$ are, independently, methyl or ethyl, or both alkenyl of 3 or 4 carbon atoms, and those in which $R^0$ is of types (c) or (d) as above defined, for which there is indicated an ability to exert a herbicidal action under controlled rates of application without substantial damage to cereals including rye and wheat. Such preferred compounds I may be therefore used as selective herbicides in cereals crops. For such selective use the preferred compounds I may be applied generally at a rate of from 1 to 5 kilograms per hectare, preferably from 1.5 to 4.5 kilograms per hectare. The preferred compounds I may be applied for such selective use pre- or post-emergence but are desirably applied post emergence both the cereal and unwanted plants.

The compounds may be employed as herbicidal compositions in association with herbicide carriers. Such compositions also form part of the present invention.

Herbicidal compositions may be employed in either solid or liquid application forms. Solid forms, e.g. dusting forms and granulates, may be produced by mixing or impregnating solid herbicide carriers such as diatomaceous earth, kaolin, talc, chalk, limestone and cellulose powder, with the compounds.

Additives may be employed in the herbicidal composition. Typical of such additives are wetting and dispersing agents, e.g. the condensation product of formaldehyde with naphthalene sulphonate and alkyl benzene sulphonates, adhesion imparting agents, e.g. dextrin, and emulsion stabilizers, e.g. ammonium caseinate. Such additives are suitable for incorporation into, e.g. a wettable powder form of composition or together with suitable solvents, e.g. hydrocarbons such as benzene, toluene, xylene, tetrahydronaphthalene, alkylated naphthalenes, kerosene, aromatic petroleum hydrocarbon fractions (e.g. commercial product Shellsol AB having b.pt. range 187°-213° C.) ketones such as isophorone, acetone, cyclohexanone, diisobutylketone and methylethylketone, alcohols such as isopropanol, ethanol, and methylcyclohexanol, chlorinated hydrocarbons such as tetrachloroethylene, ethylene chloride or trichloroethylene, to form emulsion concentrates.

The herbicidal compositions may contain, aside from a compound of formula I as active agent, other active agents, such as herbicides, e.g. of the urea class, halogen benzonitriles, carbamates and triazines.

Concentrate forms of composition generally contain between 2 and 80%, preferably between 5 and 70%, by weight of a compound of formula I as active agent.

Application forms of composition generally contain between 0.01 and 10%, by weight of a compound of formula I as active agent.

Specific examples of herbicidal compositions are described below:

EXAMPLE A

Wettable Powder 25 parts of a compound of formula I, e.g. 6-chloro-2-dimethylamino-4H-3,1-benzoxazine, or its hydrobromide salt, 7-chloro-2-dimethylamino-4H-3,1-benzoxazine or 2-tert.-butylamino-6-chloro-4H-1,3-benzoxazine, 5 parts of a condensation product from formaldehyde and naphthalene sulphonate, 2 parts of alkyl benzene sulphonate, 5 parts of dextrin, 1 part of ammonium caseinate and 62 parts of diatomaceous earth are mixed until a homogeneous mixture is obtained and then ground until the particles are considerably smaller than 45 microns as an average.

EXAMPLE B

Emulsion Concentrate 25 parts of a compound of formula I, e.g. 6-chloro-2-dimethylamino-4H-3,1-benzoxazine, 7-chloro-2-dimethylamino-4H-3,1-benzoxazine or its hydrobromide salt, or 6-chloro-2-(N-methyl-N-cyanoethylamino)-4H-1,3-benzoxazine, 65 parts of xylene and 10 parts of the mixed reaction product of an alkylphenol with ethylene oxide and calciumdodecylbenzene sulphonate are thoroughly mixed until a homogeneous solution is obtained. The resulting emulsion concentrate is diluted with water before use.

EXAMPLE C

Granulate 5 kg of a compound of formula I, e.g. 6-chloro-2-dimethylamino-4H-1,3-benzoxazine or its hydrobromide, 7-chloro-2-dimethylamino-4H-1,3-benzoxazine, or 2-tert.-butylamino-6-chloro-4H-1,3-benzoxazine are dissolved in 25 l methylene chloride. The solution is then added to 95 kg of granulated attapulgate (mesh size 24/48 mesh/inch) and thoroughly mixed. The solvent is then evaporated off under reduced pressure with warming.

The method of the present invention is preferably directed to the herbicidal use of the compounds of formula I having one or a combination of the characteristics: (1) one of A and B is halo (particularly chloro) and the other is a hydrogen atom; and more particularly A and B are at positions 6 and 7; and (2) $R^0$ is (i) either of type (a) in which $R^1$ and $R^2$ are both methyl, (ii) type (c) or (iii) type (d), (particularly where $R^4$ is methyl and n is 2); and (3) when the compound is in salt form, that salt is a hydrobromide.

The following examples are further illustrative of the invention. In the examples, all temperatures are centigrade and room temperature is 20° to 30° C., unless indicated otherwise.

EXAMPLE 1

6-chloro-2-dimethylamino-4H-3,1-benzoxazine (and hydrobromide salt)

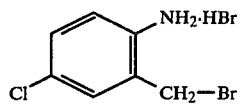

Step A, 2-hydroxymethyl-4-chloroaniline

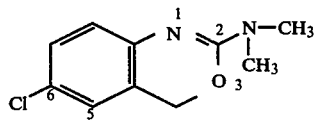

10.6 g (0.26 M) of lithium aluminum hydride are added slowly to 500 ml of tetrahydrofuran freshly dried over molecular sieve. At a temperature of 50° to 60° 34.4 g (0.2 M) of 5-chloroanthranilic acid is added in small portions every 5 to 10 minutes over a period of 3 hours. The temperature of the mixture is then allowed to decrease to room temperture and is then stirred for 16 hrs. The reaction mixture is then cooled to 0° to 5° and 12 ml. of water slowly added at 0° to 5°. 12 ml of 20% aq. sodium hydroxide are then added slowly at 0° to 5°. The resulting mixture is then stirred for ½ hr. at 0° to 5°. 18 ml of water are then added slowly, the mixture stirred for ½ hr, and then filtered. The recovered solids are slurried in 200 ml of tetrahydrofuran, the mixture heated to reflux and filtered. The filtrates are concentrated by evaporating off solvent. The residue is crystallized from toluene to yield 2-hydroxymethyl-4-chloroaniline m.p. 104°–106°.

Step B - 2-bromomethyl-4-chloroaniline hydrobromide

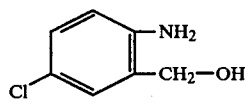

3.1 g of 2-hydroxymethyl-4-chloroaniline are added to 40 ml of 48% hydrobromide acid and the mixture heated to 100°. The mixture is stirred at 100° for ½ hr., cooled to 0° and filtered to obtain 2-bromomethyl-3-chloroaniline hydrobromide which is then air dried under dry nitrogen gas. The product is hydroscopic so is stored in a desicator, m.p. 190°–195° (decomposed and turned red).

Step C - 2-bromomethyl-4-chlorophenylisocyanate

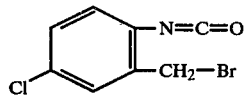

2.3 g of 2-bromomethyl-3-chloroaniline hydrobromide are added to 30 ml. of 12% phosgene in benzene. The mixture is heated to reflux in a 250 ml. flask fitted with a Dean-Stark trap and condenser. Small amounts of phosgene/benzene are carefully added until the hydrobromide is no longer detected (as indicated by following the reaction on thin layer chromatographic plates). The benzene solvent is removed from the reaction mixture by evaporation, then the 2-bromomethyl-4-chloroisocyanate product is recovered by vacuum distillation (at about 50° to 56° at about 0.05 to 0.03 mm Hg).

Step D - 6-chloro-2-dimethylamino-4H-3,1-benzoxazine hydrobromide 2 g (0.008 M) of 2-bromomethyl-4-chlorophenylisocyanate is dissolved in 50 ml. of toluene. To the solution in a reaction vessel, is slowly added 0.36 g (0.008 M) of dimethylamine in 20 ml of toluene with stirring; maintaining the temperature of from 35° to 40° (over a period of about 6 hours) resulting in the separation of the crude title product as the hydrobromide acid addition salt, which may be recovered and refined by washing with diethyl ether m.p. 183°–186°.

To obtain the title product in free base form, the crude hydrobromide salt form is added to 20 ml of toluene, to which about 20 ml of water are then added. Saturated aqueous sodium bicarbonate solution is then added, to bring the mixture to pH 8 to 9. The aqueous phase removed. The mixture (organic phase) is then washed, first with water, then brine, dried over anh. sodium sulfate and the solvent (toluene) removed by evaporation under vacuum. The residue (crude free base) is then crystallized from toluene/hexane (3:2) to yield refined title product, m.p. 97°-100°.

EXAMPLE 2

Following the procedure of Example 1, but in step D, in place of the dimethylamine used therein, using an approximately equivalent amount of:

(a) morpholine;
(b) diethylamine;
(c) piperidine;
(d) pyrrolidine;
(e) diallylamine; and
(f) diisopropylamine;

there is accordingly obtained (a) 6-chloro-2-morpholino-4H-1,3-benzoxazine (HBr, m.p. 175°-178°; free base, m.p. 121°-124°);
(b) 6-chloro-2-diethylamino-4H-1,3-benzoxazine (HBr, 122°-130°; free base 44°-47°);
(c) 6-chloro-2-piperidino-4H-1,3-benzoxazine (free base, m.p. 90°-93°).
(d) 6-chloro-2-pyrrolidino-4H-1,3-benzoxazine (HBr, m.p. 190°-194°, free base, m.p. 119°-122°);
(e) 6-chloro-2-diallylamino-4H-1,3-benzoxazine (HBr, m.p. 104°-107°; free base is an oil); and
(f) 6-chloro-2-diisopropylamino-4H-1,3-benzoxazine (HBr, m.p. 165°-190°; free base, m.p. 72°-79°).

EXAMPLE 3

7-chloro-2-dimethylamino-4H-1,3-benzoxazine (and hydrobromide salt)

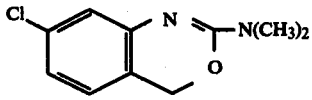

Step A - 2-hydroxymethyl 5-chloroaniline*

*may also be called 2-amino-4-chlorobenzyl alcohol

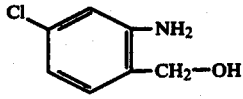

To a 500 ml vessel equipped with a mechanical stirrer is added 220 ml of tetrahydrofuran (freshly distilled from lithium aluminum hydride). The mixture is cooled to 0°, and 6 g of lithium aluminum hydride is then slowly added to the mixture. The temperature of the mixture is maintained at 0° to 20°, while 17.159 g of 4-chloroanthranilic acid is slowly added in small portions to the mixture (vented to atmosphere). The mixture is then, slowly warmed to room temperature, then refluxed for 16 hrs. The mixture is then cooled to 0° in an ice bath and 6 ml. of water slowly added (causing evolation of hydrogen). From 6 to 8 ml of 20% aqueous sodium hydroxide are then added to the mixture dropwise. The mixture becomes thicker and more difficult to stir, and a solid form upon addition of 18 ml of water (at 0°). 70 ml of tetrahydrofuran is added and the mixture stirred at room temperature for 2 hrs. The solids are recovered by filtration, digested in 100 ml of tetrahydrofuran and filtered again; the filtrates being retained and combined, then concentrated to obtain white solids. The solids are triturated with hot toluene and filtered.* The filtrate upon cooling and addition of petroleum ether, yields 2-hydroxymethyl-5-chloroaniline m.p. 104°-105°.

*The remaining solids are mostly unreacted 4-chloroanthranilic acid, which is only slightly soluble in toluene.

Step B - 2-bromomethyl-5-chloroaniline hydrobromide

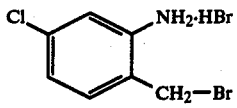

2.8 g of 2-hydroxymethyl-4-chloroaniline is added to 50 ml of hydrobromic acid (48% HBr in water). The resulting mixture is heated to 100° C., and maintained at that temperature range for 1 hr. during which period the hydro bromide forms begin to precipitate, and 30 ml. of addition 48% hydrobromic acid is added to facilitate stirring. The mixture is then cooled (to 20°), and filtered to obtain solids which are washed with 10 ml of 48% hydrobromic acid at 5° to 10°, then washed 3 times with diethylether (20 ml portions) and dried under dry nitrogen gas sweep, to obtain 2-bromomethyl-5-chloroaniline hydrobromide, which product is hydroscopic so is stored in desicator.

Step C - 2-bromomethyl-5-chlorophenylisocyanate

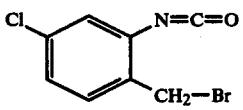

6.32 g of 2-bromomethyl-5-chloroaniline hydrobromide is added to 30 ml of benzene containing 12.5% phosgene (w/v) and the mixture refluxed in a vessel equipped with a Dean-Stark trap and additional phosgene/benzene added for a total of 250 ml (over a period of 6 hrs; ½ ml of water collected in the trap). The reaction mixture is cooled to 20°, insolubles removed by filtration and the filtrate concentrated (solvent removed), then distilled under vacuum to obtain 2-bromomethyl-5-chlorophenylisocyanate (distills at 0.05 mm Hg/50°). Further distillation yields 2-bromomethyl 4-bromo-5-chlorophenyl isocyanate (which may be refined by crystallization from petroleum ether, m.p. 48°-50°) which is useful as an intermediate in Examples 4 and 5 in preparing 6-bromo-7-chloro-4H-1,3-benzoxazine analogs of the title product of this example.

Step D, 7-chloro-2-dimethylamino-4H-1,3-benzoxazine

Repeating the procedure of Step D of Example 1, but using in place of the 2-bromomethyl-4-chlorophenylisocyanate used therein, an approximately equal amount of 2-bromomethyl-5-chlorophenylisocyanate, there is accordingly obtained 7-chloro-2-dimethylamino-4H-1,3-benzoxazine hydrobromide (m.p. 173°-176°) which is converted to its free base form (m.p. 118°-120°) in the same manner as described in Step D of Example 1.

EXAMPLE 4

6-bromo-7-chloro-2-dimethylamino-4H-1,3-benzoxazine

Following the procedure of Example 1, but using in place of the 5-chloroanthranilic acid used in Step A thereof an approximately equivalent amount of 5-bromo-4-chloroanthranilic acid, there is accordingly obtained the title product in hydrobromide salt form (m.p. 203°–207°), which is converted to its free base in the manner described in Step D of Example 1.

EXAMPLE 5

Repeating the procedure of Example 4, but in place of the dimethylamine used therein, using an approximately equivalent amount of (a) diethylamine; or
(b) morpholine;

there is accordingly obtained respectively;

(a) 6-bromo-7-chloro-diethylamino-4H-1,3-benzoxazine (HBr, m.p. 174°–177°; free base, m.p. 47°–51°); and
(b) 6-bromo-7-chloro-morpholino-4H-1,3-benzoxazine (HBr salt, m.p. 180°–184°; free base, 137°–141°).

EXAMPLE 6

2-Tertiary-butylamino-6-chloro-4H-1,3-benzoxazine (and hydrobromide salt)

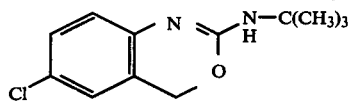

9.8 g (0.04 M) of 2-bromomethyl-4-chlorophenylisocyanate is added to 150 ml of toluene, and the mixture heated to 40°. To the mixture is added 2.8g (0.04 M) of tertiary butylamine, over a period of 5 hrs. Solids precipitate. The mixture is added to stand at room temperature for 16 hrs. The mixture is then cooled to +10° to 15°, solid recovered by filtration, washed with diethylether and dried under high vacuum to obtain the hydrobromide of the title product, m.p. 153° to 157° (decomposes at 157° to 170°).

Treating the hydrobromide in the manner described in Step D of Example 1, the title compound in free base form is obtained, m.p. 80°–83°.

EXAMPLE 7

6-chloro-2-(N-methyl, N-cyanoethylamino)-4H-1,3-benzoxazine (and hydrobromide salt)

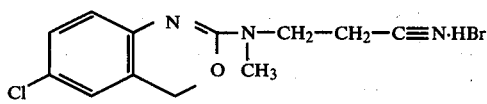

Following the procedure of Step D of Example 1, but replacing the dimethyl amine used therein with an approximately equivalent amount of N-methyl, N'-cyanoethylamine, and carrying out the reaction at 45° to 50° C. for 16 hours, the crude title product is similarly obtained which is refined by washing twice with toluene and three times with diethylether, m.p. 172°–174°.

The title salt may be converted in the manner described in Step D of Example 1, to its free base form which is obtained as an oil which solidifies under high vacuum to a white solid, m.p. 89°–93°.

EXAMPLE 8

7-chloro-2-(p-methyl-piperazinyl)-4H-1,3-benzoxazine (and hydrobromide salt)

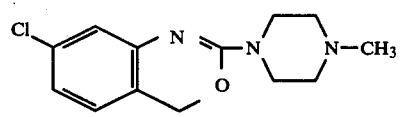

Repeating the procedure of Example 3, but in Step D, in place of the dimethylamine used therein, using an approximately equivalent amount of 4-methylpiperazine, there is accordingly obtained the hydrobromide salt form of the title compound (m.p. 217°–221°) which is converted to its free base form in the manner described in Step D of Example 1.

EXAMPLE 9

Carrying out the procedures of Examples 4 and 5, but employing 2-bromomethyl-4-bromo-5-chlorophenylisocyanate as compound II (in appropriate amounts) in place of the 2-bromomethyl-4-chlorophenylisocyanate of Step D of Example 1, the products of Examples 4 and 5 are obtained.

EXAMPLE 10

6-chloro-2-dimethylamino-4H-3,1-benzoxazine

Step A, 5,α-dichloro-2-tolylisocyanate*

*may also be called 4-chloro-2-chloromethyl-1-isocyanatobenzene.

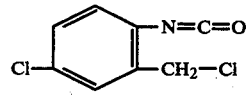

Anhydrous chlorine gas is bubbled through 167.5 grams of 5-chloro-2-tolyl isocyanate at 120° to 130° C. under irradiation of a 200 watt bulb until 43 grams of chlorine is consumed. The reaction mixture is fractionally distilled under vacuum to first remove the starting material, 5-chloro-2-tolyl isocyanate, and then recover the desired 5,α-dichloro-2-tolyl isocyanate.

Step B - 1,1,-dimethyl-3-[2-(5,α-dichlorotolyl)]urea**

**may also be called N-[(4-chloro-2-chloromethyl)phenyl]-N,N'-dimethyl urea.

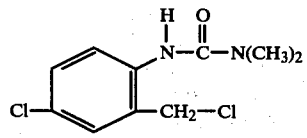

to 20.11g (0.1M) of 5, α-dichloro-2-tolylisocyanate in 200 ml of toluene is slowly added (over a period of about 3 hours) 5.0g (0.11M) of dimethylamine in 50 ml of toluene at room temperature with stirring, resulting in precipitation of crude product. The reaction mixture is stirred for an additional 30 minutes, and then filtered and the recovered solids washed twice with 100 ml. portions of toluene, then twice with 100 ml portions of diethylether to obtain 1,1-dimethyl-3-[2-(5,α-dichlorotolyl)] urea.

Step C - 6-chloro-2-dimethylamino-4H-3,1-benzoxazine

To 2.47 g (0.01 M) of 1,1-dimethyl-3-[2-(5,α-dichlorotolyl)] urea in 50 ml. of acetone is added 0.82 g (0.01 M) of sodium acetate and the mixture heated gradually to reflux. Refluxing is continued until thin layer chromatography indicates that the urea starting material is no longer present. The reaction mixture is then filtered and the filtrate evaporated under vacuum to obtain a residue. The residue is then dissolved in chloroform, and the solution washed with a 50 ml portion of saturated aqueous sodium bicarbonate, then water, then brine, then dried over anhydrous sodium sulfate. The thus-dried solution is then evaporated under vacuum to obtain the product as a residue which upon recrystallization from toluene/hexane (3:2) yields refined title product.

Repeating the procedure of this example but using in place of the 5-chloro-2-tolyl isocyanate, (used in Step A), an approximately equal amount of 4-chloro-2-tolyl isocyanate there is accordingly obtained as the urea intermediate, 1,1-dimethyl-3-[2-(4,α-dichlorotolyl)] urea which yields as the final product 7-chloro-2-dimethylamino-4H-3,1-benzoxazine.

Repeating the procedure of this example, but in Step C, omitting the sodium acetate, and using as solvent, ethanol (in place of acetone) the title product is obtained, but is recovered by column chromatography as a mixture of reaction products occurs.

EXAMPLE 11

Weed control—Pre-emergence treatment

Seed dishes are filled to a depth of 6 cm with a mixture of peat culture substrate No. 1 (obtainable from Torfstreuverband G.m.b.h, 29 Oldenberg, W. Germany) and sand. The exposed surface of the peat culture and sand mixture is sprayed with 50 ml of an aqueous emulsion of a compound of test compound (formulated in accordance with Example B) and seeds of *Lepidium sativum, Agrostis alba, Cucumis sativus* and *Phaseolus vulgaris* are sown in each dish. After sowing of the seeds, the treated surface is covered with a thin layer (0.5 cm) of peat culture/sand mixture. The dishes are kept for 20 days at room temperature with 14 to 17 hours light per day.

The compounds of the formula I of the foregoing Examples 1–10 are applied in the above manner at dosages corresponding to 1.5 kg/ha, 2.5 kg/ha and 5.0 kg/ha.

Herbicidal activity is observed, that is to say, significant damage to the test plants is observed.

EXAMPLE 12

Weed control—Post-emergence treatment

A procedure similar to that employed in Example 11 is followed with the exception that the test compounds (herbicide) are applied when the plants are at the 2-4 leaf stage, the sowing of the plant seeds being staggered to ensure that the plants reach the 2-4 leaf stage at about the same time.

Again the compounds of Example 1–10 are applied in the above manner at dosages corresponding to 1.5 kg/ha, 2.5 kg/ha and 5.0 kg/ha. A stronger herbicidal activity is observed at each dosage rate compared to Example 11.

EXAMPLE 13

The procedure of Examples 11 and 12 is followed except that seeds of *Lolium perenne* (rye grass) are used as the test plant and the dosage rate is 7.5 kg/ha with the result that herbicidal activity, again more pronounced on the post emergence treatments, is observed.

EXAMPLE 14

The procedure of Examples 11 and 12 is again repeated except that seeds of *Avena sativa* and winter wheat are sown and the title compounds of Examples 1, 2b, 2e, 3, 4, 5a and 6, 7, are evaluated, with the result that substantial damage to the plants is not observed.

What is claimed is:

1. A method of combatting plants in a plant locus, which comprises applying to the locus a herbicidally effective amount of a compound which is a free base of the formula:

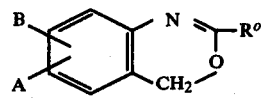

wherein each of A and B, is independently, a hydrogen atom or halo having an atomic weight of from about 34 to 80, provided that A and B are not both hydrogen atoms; and $R^0$ is a member of the class consisting of either:

(A) tertiary-amino of the formula:

wherein each of $R^1$ and $R^2$, independently, is alkyl having from 1 to 6 carbon atoms, or alkenyl having from 3 to 6 carbon atoms, provided that the ethylenically unsaturated bond is not on the carbon atom adjacent to the nitrogen atom; or (B) secondary amino of the formula:

an acid addition salt thereof.

2. A method of selectively combatting weeds in a cultivated cereal locus which comprises applying to said locus a selective herbicidally-effective amount of a compound of claim 1 in which $R^0$ is of type (A) where $R^1$ and $R^2$ are, independently, methyl or ethyl, or both alkenyl of 3 or 4 carbon atoms, or of type (B).

3. A method of claim 2 in which A and B are located at positions 6- and 7-.

4. A method of claim 1 in which A and B of the compound are located at the 6- and 7- positions.

5. A method of claim 1 in which $R^0$ of the compound is of the type (A).

6. A method of claim 5 in which each of $R^1$ and $R^2$ of the compound is alkyl.

7. The method of claim 6 in which the compound is 6-chloro-2-dimethylamino 4H-3,1-benzoxazine.

8. The method of claim 6 in which the compound is 7-chloro-2-dimethylamino-4H-3,1-benzoxazine.

9. The method of claim 6 in which the compound is 6-chloro-2-dimethylamino-4H-1,3-benzoxazine hydrobromide.

10. A method of claim 1 in which $R^0$ of the compound is of type (B).

11. The method of claim 10 which is the compound 2-tertiary-butylamino 6-chloro-4H-3,1-benzoxazine.

12. A method of claim 2 in which the compound is applied to the soil at a rate of 1 to 10 kilograms/hectare.

13. A method of claim 1 in which one of A and B of the compound is halo and the other is a hydrogen atom.

14. A method of claim 1 in which one of A and B of the compound is chloro.

15. A method of claim 1 in which $R^1$ and $R^2$ are both methyl when $R^0$ of the compound is of type (A).

16. A method of claim 1 in which the compound is a hydrobromide when the compound is a salt.

17. A method of claim 1 in which the compound is applied at a rate of from about 1.5 to 7 kilograms per hectare.

18. A method of claim 2 in which the compound is applied at a rate of from about 1 to 5 kilograms per hectare.

19. A method of claim 2 in which the compound is applied at a rate of from about 1.5 to 4.5 kilograms per hectare.

20. A method of claim 2 in which the compound is applied in a post-emergent manner.

* * * * *